United States Patent [19]

Wade et al.

[11] 4,062,953
[45] Dec. 13, 1977

[54] VARIOUS 2-SUBSTITUTED-1H-BENZ[DE]ISOQUINO-LINE-1,3(2H)-DIONES

[75] Inventors: Peter C. Wade, Pennington, N.J.; Berthold Richard Vogt, Yardley, Pa.

[73] Assignee: E. R. Squibb & Sons, Inc., Princeton, N.J.

[21] Appl. No.: 699,724

[22] Filed: June 24, 1976

[51] Int. Cl.$^2$ .................. A61K 31/47; C07D 401/08
[52] U.S. Cl. .................. 424/232; 260/281 S; 260/281 NH; 260/281 SP; 424/258
[58] Field of Search ............ 424/267 UX, 258, 232; 260/281 NH, 281 SP

[56] References Cited

U.S. PATENT DOCUMENTS

| 3,247,208 | 4/1966 | Schenker | 260/281 |
|---|---|---|---|
| 3,560,495 | 2/1971 | Frankus et al. | 260/247.1 |
| 3,625,947 | 7/1971 | Noguchi et al. | 260/281 NH |
| 3,642,836 | 2/1972 | Cusic et al. | 260/281 |
| 3,770,763 | 11/1973 | Cusic et al. | 260/281 |
| 3,935,227 | 1/1976 | Wade et al. | 260/281 NH |
| 3,940,397 | 2/1976 | Wade et al. | 260/268 TR |
| 3,940,398 | 2/1976 | Wade et al. | 260/268 TR |
| 3,947,452 | 3/1976 | Wade et al. | 260/281 NH |
| 3,959,286 | 5/1976 | Wade et al. | 260/281 NH |
| 3,996,362 | 12/1976 | Wade et al. | 424/258 |
| 3,996,363 | 12/1976 | Wade et al. | 424/258 |
| 4,006,238 | 2/1977 | Wade et al. | 424/258 |
| 4,007,191 | 2/1977 | Wade et al. | 260/288 CF |

FOREIGN PATENT DOCUMENTS

| 2,167,355 | 8/1973 | France. | |
| 2,323,555 | 8/1974 | Germany | 260/281 NH |

OTHER PUBLICATIONS

Kimura et al., Chem. Abs. 62, 11950c, (1964).

Primary Examiner—Alton D. Rollins
Assistant Examiner—Mark L. Berch
Attorney, Agent, or Firm—Lawrence S. Levinson; Merle J. Smith; Stephen B. Davis

[57] ABSTRACT

Compounds of the following formula and their acid addition salts

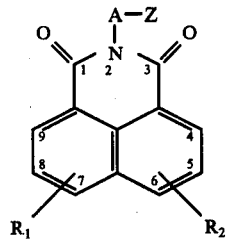

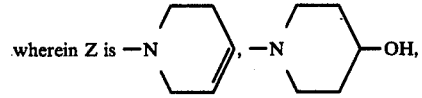

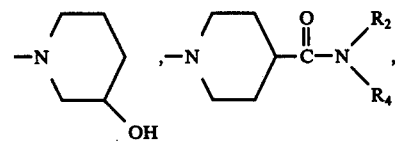

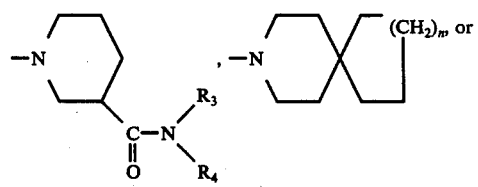

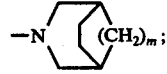

A is straight or branched chain alkylene of 2 to 6 carbons; $R_1$ and $R_2$ are located at the 7 or 8 and 5 or 6 position respectively and are independently selected from the group consisting of hydrogen, straight or branched chain alkyl of 1 to 4 carbons, straight or branched chain alkoxy of 1 to 4 carbons, Cl, Br, F, amino, nitro, cyano, and $CF_3$; $R_3$ and $R_4$ are independently selected from the group consisting of hydrogen and straight or branched chain alkyl of 1 to 4 carbons; and $n$ is 1, 2, or 3; $m$ is 1 or 2; are disclosed. These compounds possess anti-protozoal activity.

17 Claims, No Drawings

VARIOUS 2-SUBSTITUTED-1H-BENZ[DE]ISOQUINOLINE-1,3(2H)-DIONES

BACKGROUND OF THE INVENTION

1H-Benz[de]isoquinoline-1,3(2H)-diones substituted in the 2-position by a (substituted-piperidinyl or tetrahydropyridinyl)alkyl group are disclosed as possessing antidepressant, anti-anxiety, and anti-inflammatory activity in U.S. Pat. No. 3,935,227 of Wade et al. Other 2-substituted 1H-benz[de]isoquinoline-1,3(2H)-diones possessing antidepressant and anti-inflammatory activity are disclosed by Wade et al. in U. S. Pat. Nos. 3,940,397, 3,940,398, and 3,947,452.

Various naphthalimide compounds have also been developed for use as dyes and optical brightening agents. Kimura et al., for example, at Chem. Abst., Vol. 62, 11950c, disclose N-[2-piperidinoethyl]-4-methoxy-1,8-naphthalimide (i.e. 6-methoxy-2-[2-(1-piperidinyl)ethyl]-1H-benz[]isoquinoline-1,3(2H)-dione under the current Chem. Abst. nomenclature) as an optical brightening agent. Noguchi et al. in U.S. Pat. No. 3,625,947 disclose 2-[2-(2 or 4-pyridyl)ethyl]-1H-benz[de]-isoquinoline-1,3(2H)-diones as fluorescent whitening agents.

Schenker et al. in U.S. Pat. No. 3,247,208 disclose that 1-H-benz[de]isoquinoline-1,3-(2H)-diones having a (1-substituted-4-piperidinyl) group in the 2-position possess anesthetic properties. Imides having a nitroimidazolyethyl group as an N-substituent and possessing anti-bacterial and anti-protozoal activity are disclosed in U.S. Pat. Nos. 3,642,836 and 3,770,763 to Cusic et al. Certain imido dicarboxylic acid imides possessing various pharmacological properties are disclosed in U.S. Pat. No. 3,560,495 to Frankus et al.

SUMMARY OF THE INVENTION

This invention relates to new 2-substituted-1H-benz[de]isoquinoline-1,3(2H)-diones and their acid addition salts of the formula

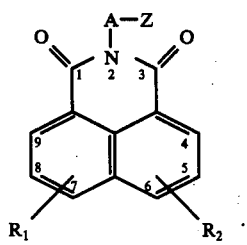
(I)

The symbols have the following meaning in formula I and throughout this specification.

$R_1$ and $R_2$ are located at 7 or 8 and 5 or 6 position respectively and are independently selected from hydrogen, straight or branched chain alkyl of 1 to 4 carbons, straight or branched chain alkoxy of 1 to 4 carbons, Cl, Br, F, amino, nitro, cyano, and $CF_3$.

A is straight or branched chain alkylene of 2 to 6 carbons.

Z is selected from

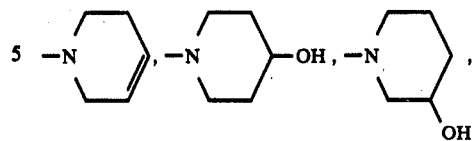

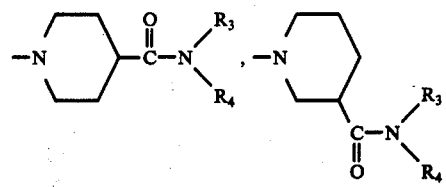

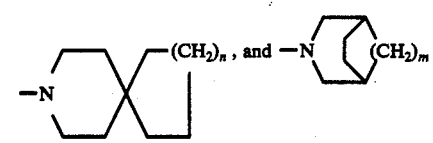

wherein $R_3$ and $R_4$ are independently selected from hydrogen and straight or branched chain alkyl of 1 to 4 carbons; $n$ is 1, 2, or 3; and $m$ is 1 or 2.

DETAILED DESCRIPTION OF THE INVENTION

The straight or branched chain alkyl groups of 1 to 4 carbons referred to throughout this specification are methyl, ethyl, n-propyl, i-propyl, n-butyl, i-butyl, and t-butyl. The straight or branched chain alkoxy groups include such alkyl groups attached to an oxygen, e.g., methoxy, ethoxy, n-propoxy, etc.

Straight or branched chain alkylene of 2 to 6 carbons is intended to include groups such as $-(CH_2)_p-$ wherein $p$ is 2 to 6,

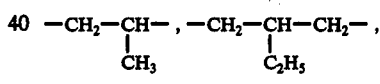

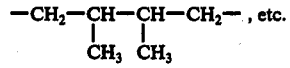

Preferred embodiments of this invention are as follows:

A is straight or branched chain alkylene of 2 to 4 carbons.

$R_1$ and $R_2$ are independently selected from hydrogen, methyl, methoxy, Cl, Br and F. $R_3$ and $R_4$ are independently selected from hydrogen and methyl.

The most preferred compounds are: $R_1$ and $R_2$ are both hydrogen.

A is straight chain alkylene of 2 to 4 carbons, especially $-CH_2-CH_2-$.

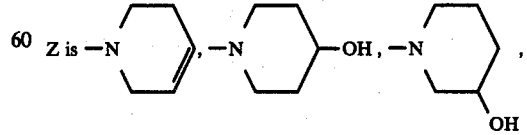

The new compounds of this invention are prepared by reacting a naphthalimide of the formula

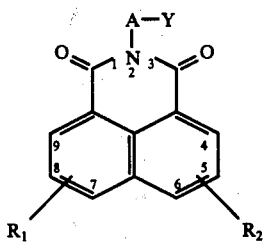

(II)

wherein $R_1$, $R_2$, and A are as defined above and Y is a leaving group such as tosylate, methane sulfonate or halogen, with a compound of the formula (III) HZ wherein Z is as defined above. This reaction is performed in a nonreactive organic solvent such as benzene, toluene, dimethylsulfoxide, etc., and with the optional presence of an organic base such as potassium carbonate. The reaction is performed by heating at about the reflux temperature for several hours.

Alternatively, the compounds of formula I can be prepared by reacting a naphthalic anhydride of the formula

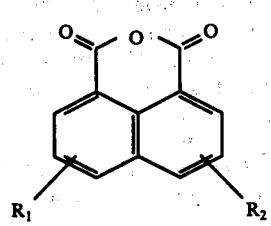

(IV)

with a compound of the formula (V) $H_2N-A-Z$ wherein $R_1$, $R_2$, A, and Z are as defined above.

The reactants of formulas II, III, IV and V are known in the art or are readily obtainable by known procedures as note the Wade et al. patents referred to above. Further process details are also provided in the illustrative examples.

The compounds of formula I wherein either or both $R_1$ and $R_2$ are amine are prepared by reducing the corresponding nitro substituted compound with a reducing agent such as hydrogen over a palladium catalyst or a suitable chemical reducing agent. This is preferably done as the last stage in the reaction procedures described above.

Depending on the reaction conditions and the starting materials used, the new compounds are obtained in the free form or in the form of their acid addition salts. The salts thereof can be converted into the free compounds in a known manner such as by reaction with a basic agent. Free bases which may be obtained can be converted into pharmaceutically acceptable acid addition salts by reaction with a variety of acids. Acids useful for preparing these acid-addition salts include, inter alia, inorganic acids, such as the hydrohalic acids (e.g. hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic, nicotinic, methanesulfonic or cyclohexanesulfamic.

The compounds of formula I possess useful anti-protozoal activity. For example, they inhibit the growth of the protozoa organism *Trichomonas vaginalis*. Thus, a compound or mixture of compounds of formula I or a pharmaceutically acceptable salts thereof can be orally administered to various mammalian species to combat such protozoa infections in an amount ranging from about 10 to about 100 mg. per kg. per day. For such purpose the compound or mixture of compounds can be formulated with a conventional excipient, vehicle, binder, preservative, etc., as called for by accepted pharmaceutical practice.

Also, the compounds of formula I wherein Z is

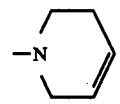

in addition to their anti-protozoal activity have activity against the organism *Staphylococcus aureas*. Thus, these compounds can also be used to combat microbial infections caused by this microorganism.

The following examples are illustrative of the invention and represent preferred embodiments. Other modifications may be readily produced by suitable variations of the reactants. All temperatures are on the centigrade scale.

EXAMPLE 1

2-[2-(3,6-Dihydro-1(2H)-pyridinyl)ethyl]-1H-benz[de]-isoquinoline-1,3(2H)-dione, hydrochloride (1:1)

a. 2-(2-Hydroxyethyl)-1-H-benz[de]-isoquinoline-1,3(2H)-dione 50 g. (0.252 mole) of naphthalic anhydride and 16 g. (0.262 mole) of ethanolamine are refluxed for three hours in 200 ml. of water (the solution is never complete). After cooling to 25° the water is decanted off and the residue recrystallized from 95% ethanol to yield 47.8 g. of 2-(2-hydroxyethyl)-1H-benz[de]isoquinoline-1,3(2H)-dione; m.p. 172°-173°.

b. 2-(2-Hydroxyethyl)-1H-benz[de]isoquinoline-1,3(2H)-dione, 4-methylbenzenesulfonate ester 52 g. (0.216 mole) of the 2-(2hydroxyethyl)-1H-benz[de]isoquinoline-1,3(2H)-dione and 100 g. (0.525 mole) of p-toluenesulfonyl chloride are added to 600 ml. of pyridine previously cooled to 5°. The mixture is shaken briefly then allowed to stand overnight at 5°. The mixture is then poured into 3000 ml. of ice and water, stirred for 15 minutes and filtered. The insoluble material is stirred with fresh water, filtered off again and dried overnight at 25° (0.1 mm.) yielding 83 g. of 2-(2-hydroxyethyl)-1H-benz[de]isoquinoline-1,3(2H)-dione, 4-methylbenzenesulfonate ester.

c. 2-[2-(3,6-Dihydro-1(2H)-pyridinyl) ethyl]-1H-benz[de]-isoquinoline-1,3(2H)-dione, hydrochloride (1:1)

20 g. (0.05 mole) of 2-(2-hydroxyethyl)-1H-benz[de]-isoquinoline-1,3(2H)-dione, 4-methylbenzenesulfonate ester from part (b) and 10 g. (0.116 mole) of 1,2,3,6-tetrahydropyridine are refluxed in 300 ml. of toluene for three hours and the mixture is then allowed to stand an additional three hours at 25°. The resulting precipitate is filtered off and washed with toluene. This toluene solution is extracted with 10% HCl, basified with 10%

NaOH, and extracted with chloroform. The chloroform solution is dried (Na₂SO₄) and the solvent removed under vacuum to yield 14.8 g. of 2-[2-(3,6-dihydro-1(2H)-pyridinyl)ethyl]-1H-benz[de]isoquinoline-1,3(2H)-dione.

14 g. of this free base are dissolved in hot absolute ethanol and treated with excess ethanolic HCl. On cooling the hydrochloride salt precipitates. This salt is filtered off and dried at 90° (50 mm.) overnight to yield 13.2 g. of 2-[2-(3,6-dihydro-1(2H)-pyridinyl)ethyl]-1H-benz[de]isoquinoline-1,3(2H)-dione, hydrochloride (1:1); m.p. 279°-281° (partial decomposition).

EXAMPLE 2

2-[2-(4-Hydroxy-1-piperidinyl)ethyl]-1H-benz[de]-isoquinoline-1,3(2H)-dione, hydrochloride (1:1)

10 g. (0.025 mole) of the 4-methylbenzenesulfonate ester from example 1(b) and 5.0 g. (0.05 mole) of 4-hydroxypiperidine are refluxed 300 ml. of toluene for three hours and the mixture is then allowed to stand an additional three hours at 25°. The resulting precipitate is filtered off. The filtrate is then extracted with 10% hydrochloric acid. The layers are separated and the aqueous layer is basified with 10% NaOH, and extracted with chloroform. The solvent is removed under vacuum and the residue is taken up in absolute ethanol and treated with excess ethanolic HCl. The resulting precipitate is filtered off, recrystallized from absolute ethanol, and dried at 90° (0.1 mm.) for three hours to yield 4.8 g. of 2-[2-(4-hydroxy-1-piperidinyl)ethyl]-1H-benz[de]isoquinoline-1,3(2H)-dione, hydrochloride; m.p. 283°-284.5° (dec.).

EXAMPLE 3

2-[2-(3-Hydroxy-1-piperidinyl)ethyl]-1H-benz[de]-isoquinoline-1,3(2H)-dione, hydrochloride (1:1)

15 g. (0.038 mole) of the 4-methylbenzenesulfonate ester from example 1(b), 4.03 g. (0.039 mole) of 3-hydroxypiperidine, and 4.9 g. (0.038 mole) of diisopropylethylamine are refluxed in 500 ml. of toluene for 1.5 hours. The reaction mixture is cooled and shaken with 10% aqueous KOH. The toluene layer is washed with water (2 × 50 ml.) an extracted with 10% hydrochloric acid (2 × 250 ml.). The acid layers are combined, basified with KOH pellets and extracted with chloroform (2 × 250 ml.). The chloroform extracts are combined, washed with water (2 × 100 ml.), dried (Na₂SO₄), and the solvent removed under vacuum. The residue is dissolved in hot isopropanol and treated with excess ethanolic HCl. The resulting precipitate is filtered off, recrystallized from ethanol, and dried at 80° under a vacuum to yield 5.9 g. of 2[2-(3-hydroxy-1-piperidinyl)ethyl]-1H-benz[de]isoquinoline-1,3(2H)-dione, hydrochloride (1:1); m.p. 289°-290° (dec.).

EXAMPLES 4-22

Following the procedure of example 1(c) but employing the 4-methylbenzenesulfonate shown in Col. I one obtains the final product shown in Col. II.

| | | Col. I | | Col. II | |
|---|---|---|---|---|---|
| | | | R₁ | | R₂ |
| Ex. | A | 7 | 8 | 5 | 6 |
| 4 | —(CH₂)₃— | H | H | H | H |
| 5 | —(CH₂)₄— | H | H | H | H |
| 6 | —(CH₂)₅— | H | H | H | H |
| 7 | —(CH₂)₆— | H | H | H | H |
| 8 | —CH—CH₂—<br>   \|<br>   CH₃ | H | H | H | H |
| 9 | —CH₂—CH—CH₂—<br>         \|<br>         CH₃ | H | H | H | H |
| 10 | —CH—CH—CH₂—<br>   \|      \|<br>   CH₃  CH₃ | H | —CF₃ | H | H |
| 11 | —(CH₂)₃— | Cl | H | H | H |
| 12 | —(CH₂)₃— | H | —CH₃ | H | H |
| 13 | —(CH₂)₃— | —OCH₃ | H | H | H |
| 14 | —CH—CH₂—<br>   \|<br>   CH₃ | —NO₂ | H | H | H |
| 15 | —CH₂—CH—CH₂—<br>         \|<br>         CH₃ | —CN | H | H | H |
| 16 | —(CH₂)₃— | Cl | H | H | Cl |
| 17 | —(CH₂)₃— | H | Br | H | H |
| 18 | —(CH₂)₃— | t-C₄H₉ | H | H | H |
| 19 | —(CH₂)₃— | H | —OC₂H₅ | H | H |
| 20 | —(CH₂)₃— | —CH₃ | H | H | —CH₃ |
| 21 | —CH—CH₂—<br>   \|<br>   CH₃ | H | Cl | Cl | H |
| 22 | —(CH₂)₃— | H | F | H | H |

Similarly, by employing the 4-methylbenzenesulfonate ester of examples 4–22 within the procedure of examples 2 and 3, other compounds within the scope of the invention are obtained.

EXAMPLE 23

2-[2-(3-Azaspiro[5.5]undecan-3-yl)ethyl]-1H-benz[de]-isoquinoline-1,3(2H)-dione, hydrochloride (1:1)

10.0 g. (0.025 mole) of the 4-methylbenzenesulfonate ester from example 1(a), 4.06 g. (0.026 mole) of 3-azaspiro[5.5]undecane, and 3.27 g. (0.025 mole) of diisopropylethylamine are refluxed in 500 ml. of toluene for three hours. The reaction mixture is cooled and washed with 10% KOH and water. The toluene solution is shaken with 10% HCl for one hour. The resulting precipitate is filtered from the two phases and recrystallized from a mixture of ethanol and dioxane to yield 2.9 g. of 2-[2-(3-azaspiro[5.5]undecan-3-yl)ethyl]-1H-benz[- de]isoquinoline-1,3(2H)-dione, hydrochloride (1:1); m.p. 290°-292° (dec.).

EXAMPLES 24-25

Following the procedure of example 23 but substituting for 3-azaspiro[5.5]undecane an equivalent amount of one of the following:
8-azaspiro[4.5]decane and
3-azaspiro[5.6]dodecane one obtains:
2-[2-(8-azaspiro[4.5]decan-8-yl)ethyl]-1H-benz[de]-isoquinoline-1,3(2H)-dione, hydrochloride and 2[2-(3-azaspiro[5.6]dodecan-3-yl)ethyl]-1H-benz[de]-isoquinoline-1,3(2H)-dione, hydrochloride; respectively.

Also, by employing the 4-methylbenzenesulfonate esters shown in Col. I of examples 4-22 within the procedure of examples 23 to 25, other compounds within the scope of the invention are obtained.

EXAMPLE 26

2-[2-(3-Azabicyclo[3.2.2]nonan-3-yl)ethyl]-1H-benz[-de]-isoquinoline-1,3(2H)-dione, hydrocholoride (1:1)

10 g. (0.025 mole) of the 4-methylbenzenesulfonate ester of example 1(b), 3.32 g. (0.027 mole) of 3-azabicyclo[3.2.2]nonane, and 3.27 g. (0.025 mole) of diisopropylethylamine are refluxed in 500 ml. of toluene for three hours. The reaction mixture is then cooled, washed with 10% KOH and water. The resulting toluene solution is shaken with 10% HCl and the resulting precipitate is filtered from the two phases. This salt is dissolved in a minimum of hot methanol, precipitated with ether, filtered, and dried at 80° under vacuum to yield 4.45 g. of 2-[2-(3-azabicyclo[3.2.2]nonan-3-yl)ethyl]-1H-benz[de]isoquinoline-1,3(2H)-dione, hydrochloride (1:1); m.p. 301°-302° (dec.).

EXAMPLE 27

2-[2-(3-Azabicyclo[3.2.1]-octan-3-yl)ethyl]-1H-benz[-de]-isoquinoline-1,3(2H)-dione, hydrochloride Following the procedure of example 26 but substituting for the 3-azabicyclo[3.2.2]-nonane and equivalent amount of 3-azabicyclo[3.2.1]octane, one obtains the titled compound.

Similarly, by employing the 4-methylbenzenesulfonate esters shown in Col. I of examples 4-22 within the procedure of examples 26 and 27, other compounds within the scope of the invention are obtained.

EXAMPLE 28

1-[2-(2,3-Dihydro-1,3-dioxo-1H-benz[de]isoquinolin-2-yl)-ethyl]-4-piperidinecarboxamide, hydrochloride (1:1)

a. 2-(2-Iodoethyl)-1H-benz[de]isoquinoline-1,3(2H)-dione 10 g. (0.042 mole) of the 2-(2-hydroxyethyl)-1H-benz[de]isoquinoline-1,3(2H)-dione from example 1(a) is refluxed in 100 g. of concentrated hydriodic acid for thirty minutes. The reaction mixture is cooled and the insoluble iodide product is filtered off, washed by slurrying with water, and filtered again. This material is then purified by digesting at reflux temperature in 1:1 chloroform-ethanol, filtering, and drying (80°, 200 mm.) for three hours to yield 10 g. of 2-(2-iodoethyl)-1H-benz-[de]isoquinoline-1,3(2H)-dione; m.p. 222°-224°.

b. 1-[2-(2,3-Dihydro-1,3-dioxo-1H-benz[de]isoquinolin-2-yl)-ethyl]-4-piperidinecarboxamide, hydrochloride (1:1)

10 g. (0.028 mole) of 2-(2-iodoethyl)-1H-benz[de]-isoquinoline-1,3(2H)-dione from part (a), 3.82 g. (0.03 mole) of isonipecotamide and 3.86 g. (0.03 mole) of diisopropylethylamine are refluxed in a mixture of 250 ml. of dioxane and 50 ml. of dimethylformamide overnight. Afterward, an additional 0.5 g. of isonipectomide and 50 ml. of dimethylformamide are added and the reaction mixture is refluxed for six more hours. After standing overnight the precipitated material is filtered off, washed with dioxane, and dried (90°) under vacuum for two hours to yield 6.8 g. of 1-[2-(2,3-dihydro-1,3-dioxo-1H-benz[de]isoquinolin-2-yl)ethyl]-4-piperidinecarboxamide; m.p. 269°-272° (dec.).

This free base is dissolved in 75 ml. of hot dimethylsulfoxide. Ethanolic HCl in 200 ml. of dioxane is added to precipitate 6.37 g. of 1-[2-(2,3-dihydro-1,3-dioxo-1H-benz[de]isoquinolin-2-yl)ethyl]-4-piperidinecarboxamide, hydrochloride (1:1); m.p. 295°-296° (dec.).

The compound of this example can also be obtained by substituting the 4-methylbenzenesulfonate ester from example 1(b) for the iodoethyl reactant in part (b).

EXAMPLES 29-35

Following the procedure of example 28 but substituting the carboxamide shown below in Col. I for the isonipecotamide one obtains the final product shown in Col. II.

| Ex. | R$_3$ | R$_4$ | position |
|---|---|---|---|
| 29 | H | H | 3 |
| 30 | —CH$_3$ | H | 3 |
| 31 | —CH$_3$ | —CH$_3$ | 4 |
| 32 | —C$_2$H$_5$ | H | 4 |
| 33 | —C$_2$H$_5$ | —C$_2$H$_5$ | 3 |
| 34 | t-C$_4$H$_9$ | H | 4 |
| 35 | i-C$_3$H$_7$ | H | 3 |

Similarly, by employing the substituted 4-methylbenzenesulfonate esters shown in Col. I of examples 2 to 22 as the reactant in examples 28 to 35, other compounds within the scope of the invention are obtained.

What is claimed is:

1. A compound of the formula

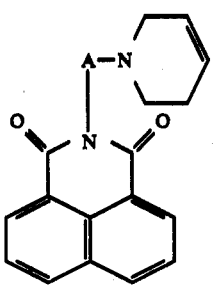

wherein A is straight chain alkylene of 2 to 4 carbons; and a pharmaceutically acceptable acid addition salt thereof.

2. A compound of the formula:

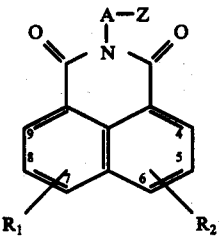

wherein Z is

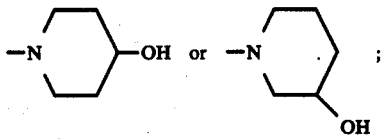

A is straight or branched chain alkylene of 2 to 4 carbons; $R_1$ and $R_2$ are located at the 7 or 8 and 5 or 6 position respectively and are independently selected from the group consisting of hydrogen, methyl, methoxy, Cl, Br, and F; and a pharmaceutically acceptable acid addition salt thereof.

3. A compound of the formula:

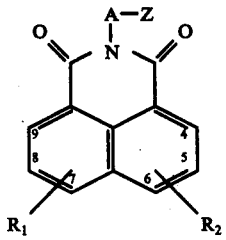

wherein Z is

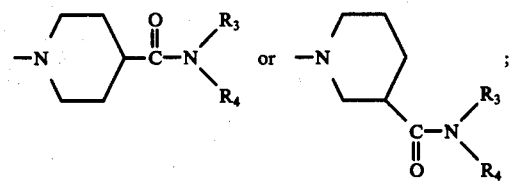

A is straight or branched chain alkylene of 2 to 4 carbons; $R_1$ and $R_2$ are located at the 7 or 8 and 5 or 6 position respectively and are independently selected from the group consisting of hydrogen, methyl, methoxy, Cl, Br, and F; $R_3$ and $R_4$ are independently selected from the group consisting of hydrogen and methyl; and a pharmaceutically acceptable acid addition salt thereof.

4. A compound of the formula:

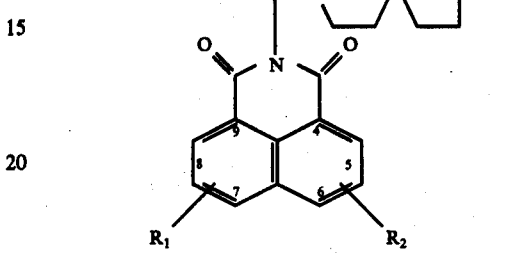

wherein $n$ is 1, 2, or 3; A is straight or branched chain alkylene of 2 to 4 carbons; $R_1$ and $R_2$ are located at the 7 or 8 and 5 or 6 position respectively and are independently selected from the group consisting of hydrogen, methyl, methoxy, Cl, Br, and F; and a pharmaceutically acceptable acid addition salt thereof.

5. A compound of the formula:

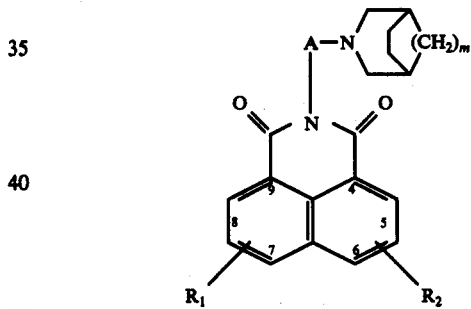

wherein $m$ is 1 or 2; A is straight or branched chain alkylene of 2 to 4 carbons; $R_1$ and $R_2$ are located at the 7 or 8 and 5 or 6 position respectively and are independently selected from the group consisting of hydrogen, methyl, methoxy, Cl, Br, and F; and a pharmaceutically acceptable acid addition salt thereof.

6. The compound of claim 1, 2-[2-(3,6-dihydro-1(2H)-pyridinyl)ethyl]-1H-benz[de]isoquinoline-1,3(2H)-dione, hydrochloride.

7. The compound of claim 2 wherein $R_1$ and $R_2$ are hydrogen and A is straight chain alkylene of 2 to 4 carbons.

8. The compound of claim 7, 2-[2-(4-hydroxy-1-piperidinyl)ethyl]-1H-benz[de]isoquinoline-1,3(2H)-dione, hydrochloride.

9. The compound of claim 7, 2-[2-(3-hydroxy-1-piperidinyl)ethyl]-1H-benz[de]isoquinoline-1,3(2H)-dione, hydrochloride.

10. The compound of claim 4 wherein $n$ is 2; $R_1$ and $R_2$ are hydrogen; and A is straight chain alkylene of 2 to 4 carbons.

11. The compound of claim 3 wherein Z is

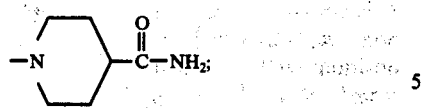

$R_1$ and $R_2$ are hydrogen; and A is straight chain alkylene of 2 to 4 carbons.

12. The compound of claim 11, 1-[2-(2,3-dihydro-1,3-dioxo-1H-benz[de]isoquinolin-2-yl)ethyl]-4-piperidinecarboxamide, hydrochloride.

13. The compound of claim 5 wherein m is 2; $R_1$ and $R_2$ are hydrogen; and A is straight chain alkylene of 2 to 4 carbons.

14. The compound of claim 13, 2[2-(3-azabicyclo[3.2.2]-nonan-3-yl)ethyl]-1H-benz[de]isoquinoline-1,3(2H)-dione, hydrochloride.

15. The compound of claim 10, 2-[2-[3-azaspiro[5.5]-undecan-3-yl]ethyl]-1H-benz[de]isoquinoline-1,3(2H)-dione, hydrochloride.

16. A pharmaceutical composition useful for treating mammals having a protozoa infection comprising a pharmaceutically acceptable carrier and a compound or mixture of compounds of the formula:

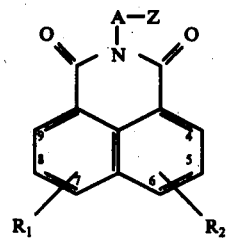

wherein Z is 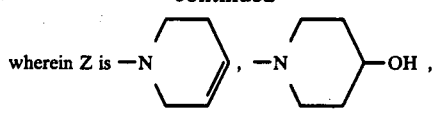

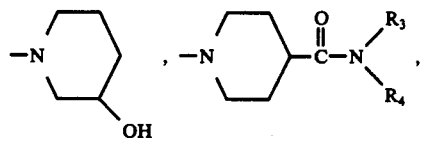

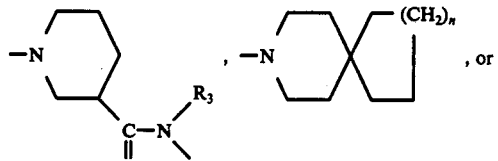

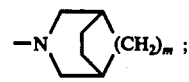

A is straight or branched chain alkylene of 2 to 6 carbons; $R_1$ and $R_2$ are located at the 7 or 8 and 5 or 6 position respectively and are independently selected from the group consisting of hydrogen, straight or branched chain alkyl of 1 to 4 carbons, straight or branched chain alkoxy of 1 to 4 carbons, Cl, Br, F, amino, nitro, cyano, and $CF_3$; $R_3$ and $R_4$ are independently selected from the group consisting of hydrogen and straight or branched chain alkyl of 1 to 4 carbons; n is 1, 2, or 3; m is 1 or 2; and a pharmaceutically acceptable acid addition salt thereof.

17. The method of treating a mammal having a protozoa infection comprising administering an antiprotozoally effective amount of the composition of claim 16.

* * * * *

UNITED STATES PATENT OFFICE
CERTIFICATE OF CORRECTION

Patent No. 4,062,953   Dated December 13, 1977

Inventor(s) Peter C. Wade et al.

It is certified that error appears in the above-identified patent and that said Letters Patent are hereby corrected as shown below:

Col. 1, line 23 after "benz" insert -- [de] --.

Col. 7, line 41, "and" should read -- an --.

Signed and Sealed this

Twenty-seventh Day of June 1978

[SEAL]

Attest:

RUTH C. MASON
Attesting Officer

DONALD W. BANNER
Commissioner of Patents and Trademarks